United States Patent [19]

Nagata et al.

[11] Patent Number: 4,723,046
[45] Date of Patent: Feb. 2, 1988

[54] PROCESS FOR THE PREPARATION OF 4,4′-BIPHENOL

[75] Inventors: Teruyuki Nagata; Tohru Miura, both of Ohmuta, Japan

[73] Assignee: Mitsui Toatsu Chemicals, Incorporated, Tokyo, Japan

[21] Appl. No.: 62,674

[22] Filed: Jun. 16, 1987

[30] Foreign Application Priority Data

Jun. 23, 1986 [JP] Japan .................. 61-144834
Aug. 8, 1986 [JP] Japan .................. 61-185221

[51] Int. Cl.$^4$ .............................. C07C 39/17
[52] U.S. Cl. .......................... 568/730; 568/718; 568/719; 568/721; 568/830
[58] Field of Search .............. 568/718, 719, 721, 822, 568/730

[56] References Cited

U.S. PATENT DOCUMENTS 2,368,361 1/1945 Jenkins .................. 260/620

OTHER PUBLICATIONS

Chemische Berichte, 22, 335 (1898).
"Journal of Organic Chemistry", 34, 1160 (1969) Allen Hay.

Primary Examiner—Werren B. Lone
Attorney, Agent, or Firm—Fisher, Christen & Sabol

[57] ABSTRACT

A process for preparing 4,4′-biphenol comprising subjecting 4,4-bis(4-hydroxyphenyl)cyclohexanol to decomposition and dehydrogenation in the presence of a dehydrogenation catalyst.

4,4-Bis(4-hydroxyphenyl)cyclohexanol is a novel compound which can be prepared by reacting 4-hydroxycyclohexanone with phenol.

10 Claims, 1 Drawing Figure

PROCESS FOR THE PREPARATION OF 4,4'-BIPHENOL

BACKGROUND OF THE INVENTION (a) Field of the Invention

The present invention relates to a novel process for the preparation of 4,4'-biphenol. It also relates to a precursor of 4,4'-biphenol, that is, 4,4-bis(4-hydroxyphenyl)cyclohexanol of the formula (I):

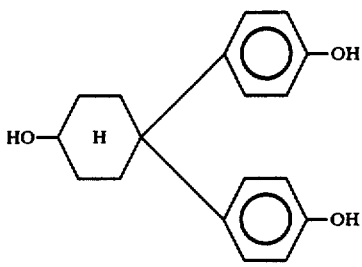

and a process for preparing the precursor.

(b) Description of the Prior Art 4,4'-Biphenol is useful as a stabilizer and a dyestuff intermediate as well as a material for the resin such as polyester, polyepoxide, polyurethane, polycarbonate and the like. In particular, it has recently attracted attention as a material for high-temperature resistant resin.

Various processes have so far been proposed for the preparation of 4,4'-biphenol. A preparation process by the diazo decomposition of benzidine has been known for a long time [Chemische Berichte, 22, 335]. Another preparing process by the alkali fusion of sodium 4,4-bisphenyldisulfonate has afterward been known [U.S. Pat. No. 2,368,361 (1942)]. In recent years a process for obtaining biphenol by the dealkylation of tetra-tert-butylphenol derived from 2,6-di-tert-butylphenol has been widely investigated and many patents have been published [Journal of Organic Chemistry, 34, 1160 (1969) etc.]. In addition, also known are processes for obtaining biphenol by the dehalogenation and dimerization of dihalogenated phenols (Japanese Patent Laid Open No. 53631/1981) and by the alkali treatment of halogenated biphenyl (Japanese Patent Laid Open No. 22347/1979). In addition, various other preparation processes have been proposed. Above-mentioned conventional processes, however, have drawbacks such as harmfulness to health or expensiveness of raw materials, problems on waste disposal, need for severe process conditions, low yield and so on.

SUMMARY OF THE INVENTION

An object of this invention is to provide a novel process for the preparation of 4,4'-biphenol.

Another object of this invention is to provide a novel compound used as a precursor in the novel preparation process of this invention, and a process for the preparation of the novel compound.

The preparation process of 4,4'-biphenol according to the present invention comprises subjecting 4,4-bis(4-hydroxyphenyl)cyclohexanol of the formula (I):

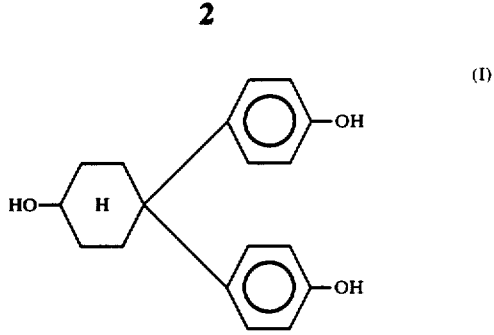

to decomposition and dehydrogenation reactions. The compound of the formula (I) is a novel compound. Although compounds having alkyl radicals on the cyclohexane ring such as 1,1-bis(4-hydroxyphenyl)cyclohexane and 4-methyl-1,1-bis(4-hydroxyphenyl)cyclohexane have been known as similar compounds, 4,4-bis(4-hydroxyphenyl)cyclohexanol have never been known.

The present inventors have succeeded in the synthesis of 4,4-bis(4-hydroxyphenyl)cyclohexanol and technically established the novel preparation process of biphenol by using the above cyclohexanol.

Figure 1:
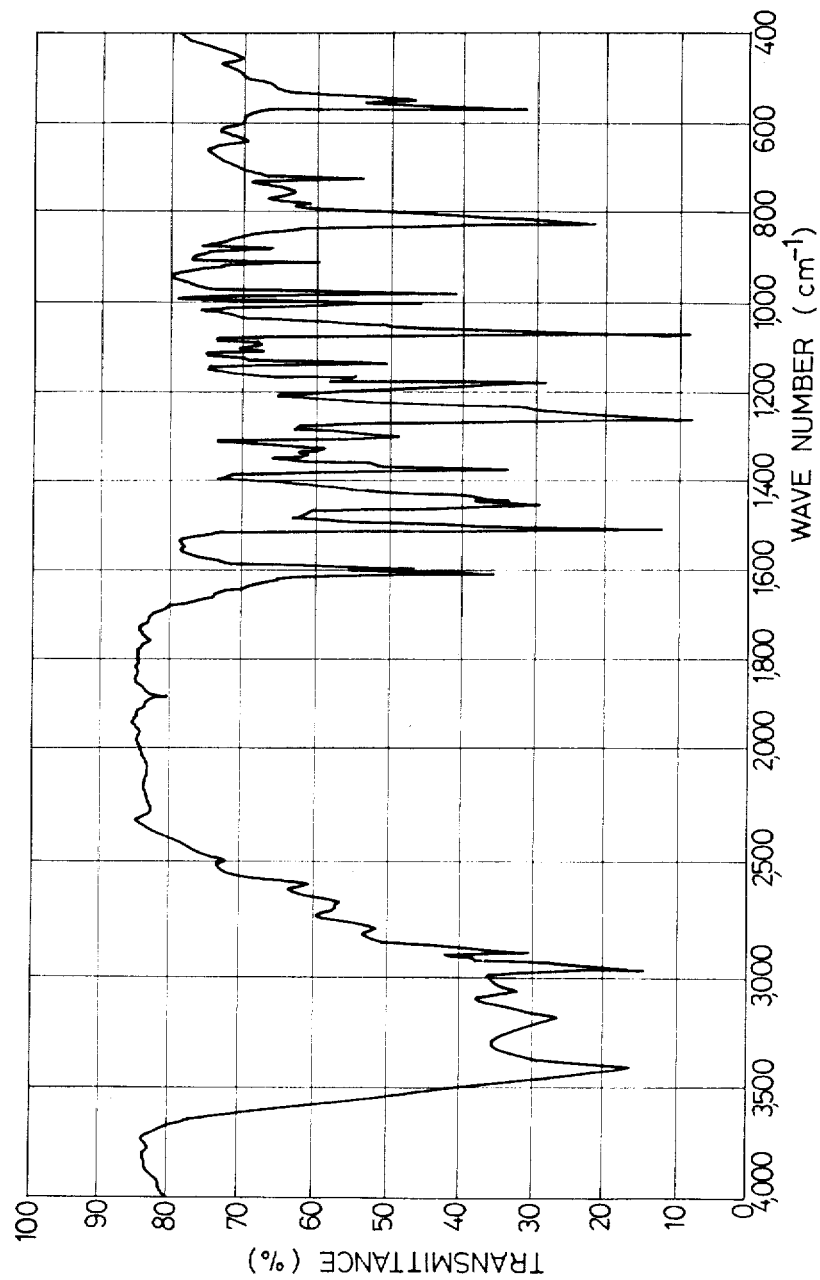
FIG. 1 illustrates the IR spectrum of the 4,4-bis(4-hydroxyphenyl)cyclohexanol obtained in Example 1.

DETAILED DESCRIPTION OF THE INVENTION 4,4-bis(4-hydroxyphenyl)cyclohexanol of the formula (I) which is the precursor of 4,4'-bisphenol in this invention can be obtained by conducting a condensation reaction of 4-hydroxycyclohexanone with phenol in the presence of an acid catalyst.

4-Hydroxycyclohexanone for use in the condensation reaction can be obtained by reacting hydroquinone with hydrogen in water in the presence of a carrier supported palladium catalyst (Japanese Patent Laid-Open No. 4932, 1982), or by oxidizing cyclohexane-1,4-diol with a chromium compound (Japanese Patent Laid Open No. 88450/1984).

Examples of the acid catalyst which may be employed in the condensation reaction include hydrochloric acid, sulfuric acid, phosphoric acid, toluenesulfonic acid, $BF_3$, $ZnCl_2$, $AlCl_3$, $SnCl_4$ and cation exchange resin having movable acid group(s).

The amount of the catalyst used is in the range of 0.1 to 30 parts by weight per 100 parts by weight of 4-hydroxycyclohexanone.

The reaction rate can further be enhanced by the addition of a co-catalyst. Examples of the co-catalyst which may accelerate the reaction include alkyl mercaptans such as methyl mercaptan, ethyl mercaptan, n-propyl mercaptan, isopropyl mercaptan, n-butyl mercaptan, isobutyl mercaptan, tert-butyl mercaptan as well as high molecular weight alkyl mercaptans.

It is also possible to use other sulfur compounds such as hydrogen sulfide, thiophenols, thioalcohols, thio acids, polymeric thioacetone, dialkyl sulfides, as well as selenium compounds which correspond to these sulfur compounds as the co-catalyst.

The condensation reaction may be carried out in a solvent which exhibits no adverse effect on the reaction. Examples of the solvent which may be employed include aromatic hydrocarbons, chlorinated aliphatic hydrocarbon and glacial acetic acid. However, in order to increase the yield of the product and minimize the occurrence of side reactions, it is desirable to use an excess of phenol as the solvent. Phenol is suitably used in an amount of 2 to 10 parts by weight per part by weight of 4-hydroxycyclohexanone.

The reaction temperature is in the range of 30° to 100° C. and preferably 40° to 70° C. The reaction temperature above this range is undesirable because the amount of by-products increases to decrease the yield of the product.

4,4-bis(4-hydroxyphenyl)cyclohexanol thus formed can be isolated as precipitates by pouring the reaction mass into a solvent which solvent slightly dissolves this compound, e.g. benzene, or the like, followed by cooling and crystallization.

4,4-Bis(4-hydroxyphenyl)cyclohexanol thus isolated is mostly or entirely in the form of phenol adducts. The phenol adducts of 4,4-bis(4-hydroxyphenyl)cyclohexanol easily dissociate phenol by heating with a solvent which neither reacts with the compound of the formula (I) nor forms the adduct with it. Suitable solvents which may be used include benzene, toluene, xylene, ethylbenzene cumene, cymene, octane, decane, dodecane and the like. In addition to phenol, the precursor of this invention can also form stable adducts with alcohols such as isopropyl alcohol, water or the like. These adducts can be dissociated by heating in the solvent in the same manner. When excess phenol is used as a solvent, the phenol adduct can be used for the material of biphenol in the next step as is. The phenol adduct can, of course, be employed after dissociating phenol.

In addition, phenol used in excess can be recovered and used again by such methods as neutralization of the mother liquor followed by filtration of the crystallized salts, or distillation of the mother liquor under reduced pressure.

In the process of this invention, 4,4'-biphenol is prepared by subjecting 4,4-bis(4-hydroxyphenyl)cyclohexanol of the formula (I) thus obtained to the decomposition and dehydrogenation reactions.

In the decomposition and dehydrogenation reaction of this invention, the decomposition and the dehydrogenation may be conducted either in a single step or in separate steps. It is particularly efficient to carry out both reactions in a single step.

The decomposition reaction is performed in the presence of a basic catalyst or an acid catalyst. Illustrative basic catalysts which may be used as efficient decomposition catalyst include alkali metal hydroxide such as sodium hydroxide potassium hydroxide, lithium hydroxide, etc.; alkaline earth metal hydroxides such as magnesium hydroxide, barium hydroxide, etc.; carbonates; acetates; phenoxide; and salts of organic weak acids.

Suitable acid catalysts which may be used include acids such as p-toluenesulfonic acid; weakly acidic salts of acid such as potassium hydrogen sulfite; and acidic metal salts such as aluminium chloride, stannous chloride etc.

Strongly basic catalysts such as sodium hydroxide are particularly preferred among these catalysts.

The amounts of these catalysts are preferably 2–40 parts by weight and more preferably 5–20 parts by weight per 100 parts by weight of 4,4-bis(4-hydroxyphenyl)cyclohexanol.

The dehydrogenation reaction is usually carried out in the presence of a dehydrogenation catalyst. Any known dehydrogenation catalysts may be used in this reaction. Examples of the catalysts include nickel catalysts such as Raney nickel, reduced nickel, nickel-carrier catalysts comprising nickel supported on diatomaceous earth, alumina, pumice, silica gel, acid clay, or other carriers; cobalt catalysts such as Raney cobalt, reduced cobalt, cobalt-carrier catalysts, etc.; copper catalysts such as Raney copper, reduced copper, copper-carrier catalysts, etc.; palladium catalysts such as palladium black, palladium oxide, colloidal palladium palladium-carbon, palladium-barium sulfate, palladium-magnesium oxide, palladium-calcium oxide, palladium-alumina, etc.; platinum catalysts such as platinum black, colloidal platinum, platinum oxide, platinum sulfide, platinum-carrier catalysts including platinum-carbon, etc.; rhodium catalysts such as colloidal rhodium, rhodium-carbon, rhodium oxide, etc.; other platinum group catalysts such as ruthenium catalysts; rhenium catalysts such as dirhenium heptoxide, rhenium carbon, etc.; copper chromium oxide catalyst; molybdenum oxide catalyst; silver catalysts, and the like.

Among these catalysts, platinum group catalysts such as palladium catalysts, platinum catalysts are preferred.

The dehydrogenation catalyst is used in an amount as the catalyst metal atom of usually 0.001 to 0.2 gram atom, preferably 0.004 to 0.1 gram atom per mol of 4,4-bis(4-hydroxyphenyl)cyclohexanol.

Although the decomposition and dehydrogenation reactions may be carried out in the absence of any hydrogen acceptor, higher yield can be obtained by combined use of the hydrogen acceptor.

Although any hydrogen acceptor may be used, several types of compounds are useful in this invention. These acceptors include, for example, ethylenically unsaturated organic compounds such as ethylene, propylene, etc.; acetylenically unsaturated organic compounds such as acetylene, methylacetylene, etc.; organic compounds containing azo groups such as azobenzene etc.; nitro or carbonyl compounds and phenolic compounds.

Among these hydrogen acceptors organic compounds containing conjugated double bonds such as styrene compounds including α-methylstyrene, nitrobenzene, maleic anhydride, methylacetylene, crotonic acid, phenol are preferred. Particularly preferred hydrogen acceptors are selected from the compounds which are highly active and also able to provide useful products after hydrogenation. For example, cumene can be obtained by employing α-methyl styrene and cyclohexanone can also be obtained by employing phenol. Both compounds may be utilized as useful materials.

The decomposition and dehydrogenation reactions are preferably conducted at a temperature of 100°–400° C., more preferably 150°–300° C. When the temperature is below 150° C., the reaction rate is too slow. On the other hand, the temperature above 300° C. is unfavorable because side reactions take place.

Although the reactions may be carried out in the gaseous phase, high temperatures of 300° C. or above are required because of the high melting points of the raw materials and products. Therefore, for the sake of yield, workability, energy saving, and the like, it is preferable to carry out the reactions in the liquid phase. In the liquid phase reactions, it is recommended to perform the reactions in the presence of a solvent. Suitable solvents which may be employed include, for example, ethers such as ethylene glycol monomethyl ether, ethylene glycol dimethyl ether, diethylene glycol monomethyl ether, tetrahydrofuran, dioxane, dipropyl ether, diphenyl ether; alcohols such as ethanol, isopropanol, ethylene glycol, diethylene glycol, triethylene glycol, propylene glycol; nitriles such as acetonitrile propionitrile, benzonitrile; aromatic hydrocarbons such as benzene, toluene, xylene, mesitylene, ethylbenzene, cumene; and the like. Water is also a preferable solvent. Moreover, the above-mentioned hydrogen acceptors may be used as the solvent.

4,4'-Biphenol formed by the process of this invention can be isolated by removing the catalyst from the resultant reaction mixture and then separating the product according to conventional procedures such as crystallization and the like.

The present invention will hereinafter be described in detail with respect to the following examples.

EXAMPLE 1

Into a 100 ml reaction flask, 11.4 g (0.10 mole) of 4-hydroxycyclohexanone, 47.1 g (0.50 mole) of phenol and 6 ml of 36% hydrochloric acid were charged and reacted at 60° C. for 4 hours. After completing the reaction, the reaction mass was poured into 300 ml of benzene. After stirring at room temperature for 2 hours, resulting crystals were filtered. The separated crystals were heated in cumene for 30 minutes under reflux to distill out phenol, and then cooled and filtered. The procedures for treating the crystals were repeated again. The separated crystals were subjected to sludging in a mixture of ethyl acetate and benzene in order to completely removing the residual cumene into the solvent layer. The mixture was filtered and dried to give 22.3 g of white crystals. Pure crystals isolated by column chromatography of the white crystals had a melting point of 218° C. and were identified with 4,4-bis(4-hydroxyphenyl)cyclohexanol according to $^1$H-NMR and IR.

Crude crystals had purity of 98% and yield of 77% at the step of separation.

Table 1 illustrates $^1$H-NMR data on 4,4-bis(4-hydroxyphenyl)cyclohexanol.

FIG. 1 shows IR absorption spectrum of the same compound.

TABLE 1

| Signal | ppm. | Assignment |
|--------|------|------------|
| a | 1.2–2.1 | Cyclohexane ring |
| b | 3.4–3.7 | |
| c | 4.0–4.1 | —OH |
| d | 6.5–6.7 | p-substituted benzene |
| e | 6.9–7.2 | |
| f | 8.7–8.8 | —OH |

Each area ratio is agreed with the proton ratio.
Solvent; Dimethylsulfoxide (DMSO)
Temperature; 80° C.

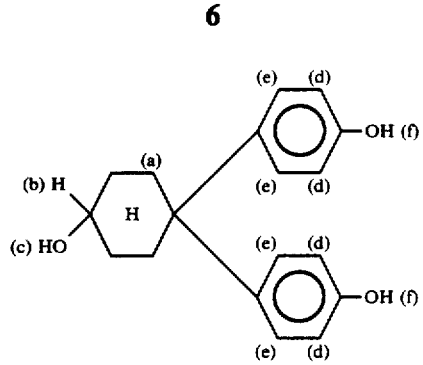

EXAMPLE 2

A 300 ml stainless steel autoclave was charged with 17.1 g (0.060 mole) of 4,4-bis(4-hydroxyphenyl)cyclohexanol, 2.6 g (0.065 mole) of sodium hydroxide, 21.3 g (0.18 mole) of α-methylstyrene, 100 g of water and 0.2 g of 5% palladium-carbon catalyst. After replacing the air inside of the autoclave with nitrogen, the mixture was reacted at 250° C. for 4 hours.

After completing the reaction, the resulting mixture was cooled. The crystals which had deposited in part was dissolved by adding 30.0 g of 20% aqueous sodium hydroxide solution and filtered to remove the catalyst. The filtrate was extracted with 100 ml of benzene to recover α-methylstyrene and cumene, followed by adding aqueous hydrochloric acid to precipitate desired product. The precipitated crystals were filtered, washed with water, and dried to give 10.8 g of crystals.

4,4'-Biphenol thus obtained had purity of 85.8% according to liquid chromatography. The impurity was p-phenylphenol. The yield of 4,4'-biphenol converted to the purity basis was 83%.

What is claimed is:

1. A process for the preparation of 4,4'-biphenol which comprises subjecting 4,4-bis(4-hydroxyphenyl)-cyclohexanol of the formula (I):

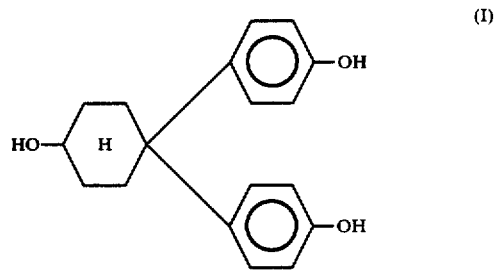

(I)

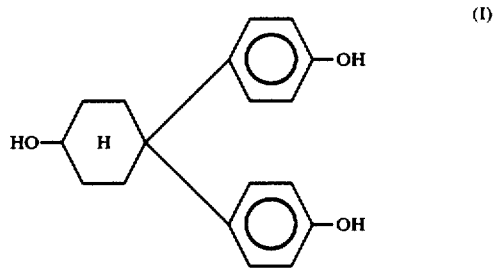

(I)

to decomposition and dehydrogenation reactions in the presence of a dehydrogenation catalyst.

2. The process as claimed in claim 1 wherein the decomposition and dehydrogenation reactions are carried out at a temperature of 100° to 400° C.

3. The process as claimed in claim 1 wherein the decomposition and dehydrogenation reactions are carried out in the presence of a hydrogen acceptor in addition to the dehydrogenation catalyst.

4. The process as claimed in claim 1 wherein the reaction is conducted in an organic solvent or water.

5. A process for the preparation of 4,4'-biphenol which comprises reacting 4-hydroxycyclohexanone with phenol in the presence of an acid catalyst to give 4,4-bis(4-hydroxyphenyl)cyclohexanol of the formula (I)

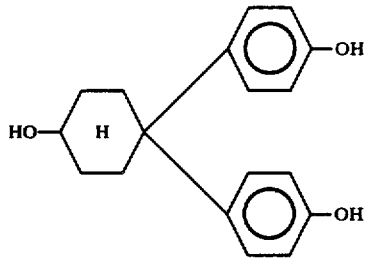

and successively subjecting 4,4-bis(4-hydroxyphenyl)-cyclohexanol to decomposition and dehydrogenation reactions in the presence of a dehydrogenation catalyst.

6. The process as claimed in claim 5 wherein the reaction of 4-hydroxycyclohexanone with phenol is conducted by using phenol as a solvent.

7. The process as claimed in claim 5 wherein the decomposition and dehydrogenation reactions are carried out at a temperature of 100° to 400° C.

8. The process as claimed in claim 5 wherein the decomposition and dehydrogenation reactions are carried out in the presence of a hydrogen acceptor in addition to the dehydrogenation catalyst.

9. The process as claimed in claim 5 wherein the decomposition and dehydrogenation reactions are carried out in an organic solvent or water.

10. 4,4-Bis(4-hydroxyphenyl)cyclohexanol of the formula (I)

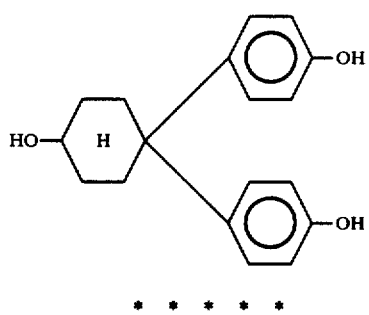

* * * * *

UNITED STATES PATENT AND TRADEMARK OFFICE
CERTIFICATE OF CORRECTION

PATENT NO. : 4,723,046

DATED : February 2, 1988

INVENTOR(S) : Nagata et al.

It is certified that error appears in the above-identified patent and that said Letters Patent is hereby corrected as shown below:

On the title page, the first foreign priority application should be corrected to read:

[30] Foreign Application Priority Data

Jun. 23, 1986 [JP]    Japan ....... 61-144734

Signed and Sealed this

Fifth Day of July, 1988

*Attest:*

DONALD J. QUIGG

*Attesting Officer*

*Commissioner of Patents and Trademarks*